Figure 1:
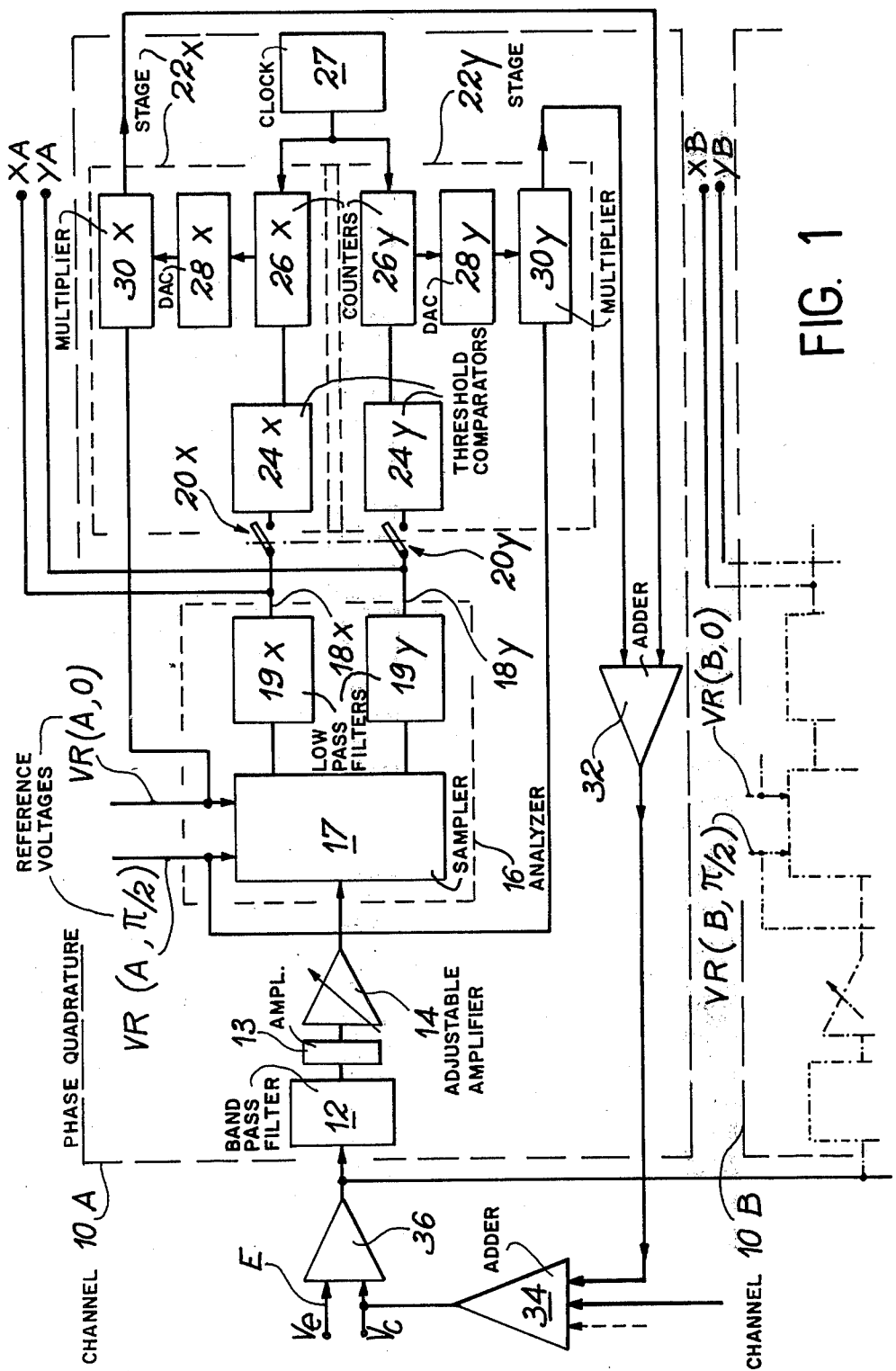

United States Patent [19]

Pigeon et al.

[11] 4,326,166
[45] Apr. 20, 1982

[54] CORRECTING CIRCUIT FOR DIFFERENTIAL PICK-UP, COMPRISING DIGITAL MEANS

[75] Inventors: Michel Pigeon, Bures sur Yvette; Robert Saglio, Antony, both of France

[73] Assignee: Commissariat a l'Energie Atomique, Paris, France

[21] Appl. No.: 100,128

[22] Filed: Dec. 4, 1979

[30] Foreign Application Priority Data

Dec. 7, 1978 [FR] France .................................. 78 344

[51] Int. Cl.³ .................... G01N 27/72; G01R 33/14
[52] U.S. Cl. ..................................... 324/225; 324/233
[58] Field of Search ............... 324/225, 233, 239–243, 324/326, 229, 339

[56] References Cited

U.S. PATENT DOCUMENTS 4,006,407 2/1977 Flaherty et al. .................... 324/233

Primary Examiner—Gerard R. Strecker
Assistant Examiner—Walter E. Snow

[57] ABSTRACT

A circuit for automatically correcting a signal given by a differential pick-up. Said circuit comprises as many corrective channels as there are frequencies in the signal. Each of said channels, comprises a band-pass filter centered to the frequency ascribed to the respective channel, an analyzer for the resistive (X) and reactive (Y) portions of the filtered voltage, two stages for the separate treatment of said two portions, each of said stages comprising a threshold comparator, a counter, a digital-analog converter, and a multiplier for multiplying by a reference-signal, either in phase (as regards portion X), or in phase-quadrature (as regards portion Y), with respect to the pick-up energization. An adder is adapted to reconstitute a corrective voltage to be substracted from the input signal.

2 Claims, 3 Drawing Figures

CORRECTING CIRCUIT FOR DIFFERENTIAL PICK-UP, COMPRISING DIGITAL MEANS

The present invention relates to a circuit for automatically correcting a signal given by an unbalanced differential pick-up. It has an application in the non-destructive testing by eddy currents and, more generally, in all cases where a signal delivered by a differential pick-up has to be measured.

It is known that testing a metal part by eddy currents consists in studying the variations of the currents induced into said part by the magnetic field of a coil along which flows an energizing alternating current. Such currents, in their turn, generate a field in opposition to the inductive field. They thus modify the impedance of the energizing coil. Said coil is arranged within a probe which is caused to move along the part to be tested. Any defect, or flaw, in said part (e.g. a change in the dimension thereof, a variation of electric conductivity, cracks) will disturb the path and/or the magnitude of eddy currents and, accordingly, will modify the coil impedance.

A probe for testing by means of eddy currents is generally constituted by two oppositely fed adjacent coils, mounted in two adjacent arms of a measuring bridge. The passage of a defect, or flaw, through the probe field causes said bridge to be unbalanced twice, first in one direction, then in the opposite direction. The voltage delivered by the probe is amplified, then analysed and it is finally represented on a cathode-ray tube screen by its resistive component (or real component) X and by its reactive component (or imaginary component) Y. The alternating voltage delivered by the probe is therefore represented by a point, the co-ordinates of which are X, Y. Whenever a defect, or flaw, passes through the probe field, said point draws a line usually with two lobes forming a slanting eight. Each of said defects can thus be identified by the inclination of said lobes with respect to a reference axis and by their amplitude.

In view of their very structure, the probes for testing by means of eddy currents often show some unbalance between the bridge two arms, so that, even in cases where the part to be tested is devoid of defects, the signal given by the probe is not strictly zero. When a defect, or flaw, is detected, the signal provided therefore comprises a portion due to the bridge unbalance, said portion being superimposed to the measurement signal proper.

Such a source of error is to be met more generally in all the devices using differential pick-ups, viz, pick-ups comprising two similar portions, the effects of which are supposed to compensate each other "at no load." The most frequent case is that of those measurement bridges used in electronics, in particular in impedance-meters and in phase-meters.

Devices capable of correcting such an error are already known. They consist of corrective circuits that are manually adjustable (e.g. by means of a potentiometer) and permit to cancel the measurement signal whenever the pick-up is exempt from any disturbance. Such a correction is maintained during the measuring operation proper, in order that the overall signal be devoid of that portion due to the pick-up unbalance.

Such corrective means provided with a potentiometer are in general use in all the devices for testing by means of eddy currents. While such devices are relatively satisfactory, however the actuation thereof is rather intricate since they require the intervention of an operator.

The present invention precisely provides a corrective circuit exempt from such a drawback, since the operation thereof is entirely automatic.

More specifically, the object of the present invention is to provide a circuit for automatically correcting an electric signal given by a differential pick-up likely to be slightly unbalanced, said output signal thus containing a portion due to said unbalance, said circuit being of the type comprising means for determining that portion and extracting it from the signal given by a said pick-up, said circuit being characterized in that said means contain as many corrective channels as there are components with different frequences in said signal, each of said channels comprising:

(a) a band-pass filter centered to one of said frequencies, followed by an adjustable gain amplifier;

(b) an analyzer fed by a reference-voltage at said frequency and by a voltage in phase-quadrature (i.e. shifted by 90°) with respect to said reference-voltage, on the one hand, and by the voltage delivered by said band-pass filter, on the other hand, said analyzer delivering two DC-voltages X and Y proportional to the two components of the filtered signal, in phase and in phase quadrature with respect to said reference-voltage, respectively;

(c) a first stage comprising: a threshold comparator fed by voltage X; a counter-back counter connected to said comparator; a clock for feeding said counterback counter; a digital-analog converter connected to said counter; a multiplier with two inlets and one outlet, one of said inlets being fed by said reference voltage, while the other is connected to said converter;

(d) a second stage comprising: a threshold comparator fed by voltage Y; a counter-back counter connected to said comparator; a clock for feeding said counter-back counter, a digital-analog converter connected to said counter-back counter; a multiplier with two inlets and one outlet, one of said inlets being fed by said voltage in phase-quadrature with respect to said reference-voltage, while the other inlet is connected to said converter;

(e) an adder with two inlets and one outlet, one of said inlets being connected to the first stage multiplier outlet, while the other inlet is connected to the second stage multiplier, outlet, the outlet of said adder connected to the circuit inlet by means of a phase-inverter in common for all said channels.

Figure 2:
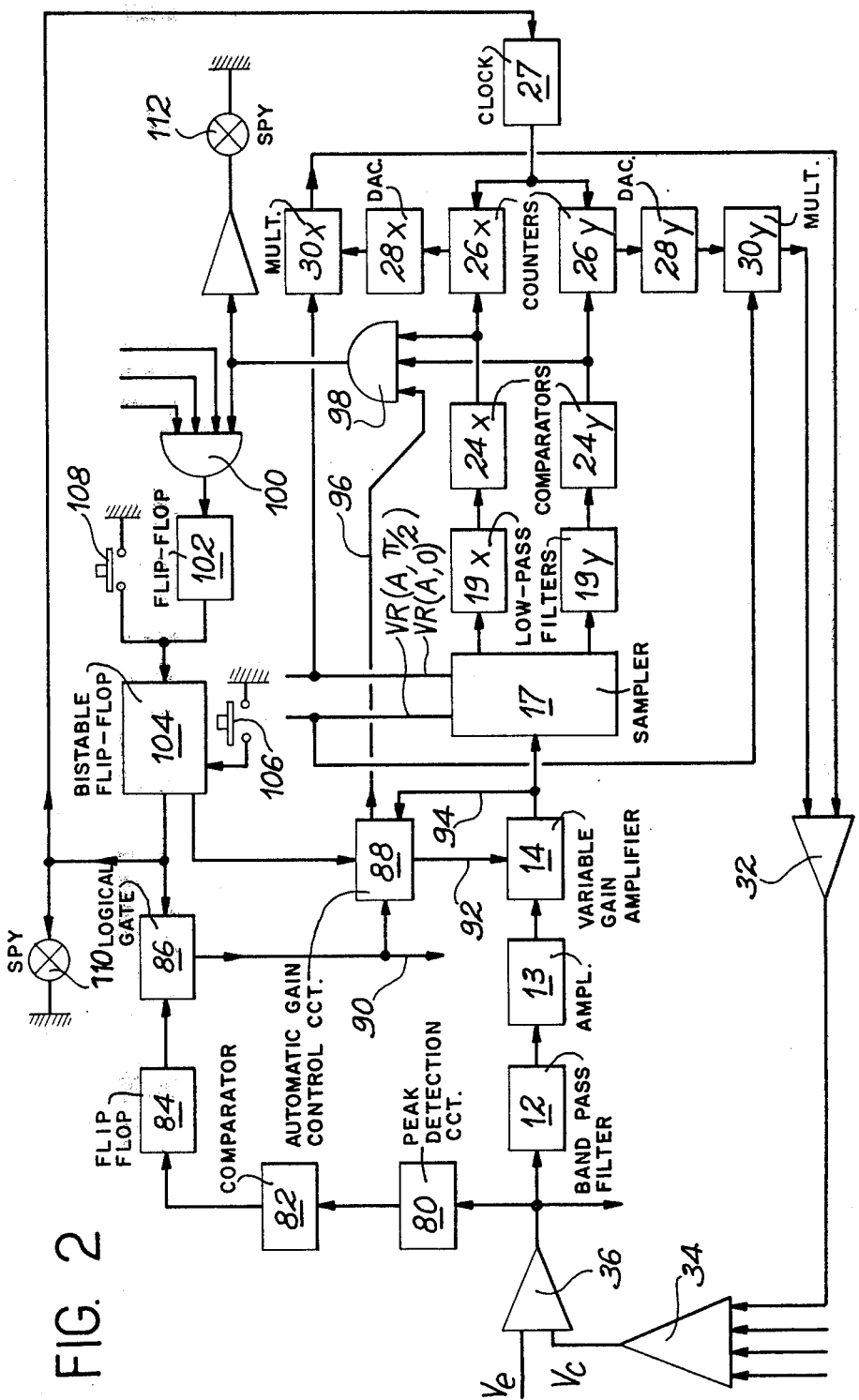
Figure 3:
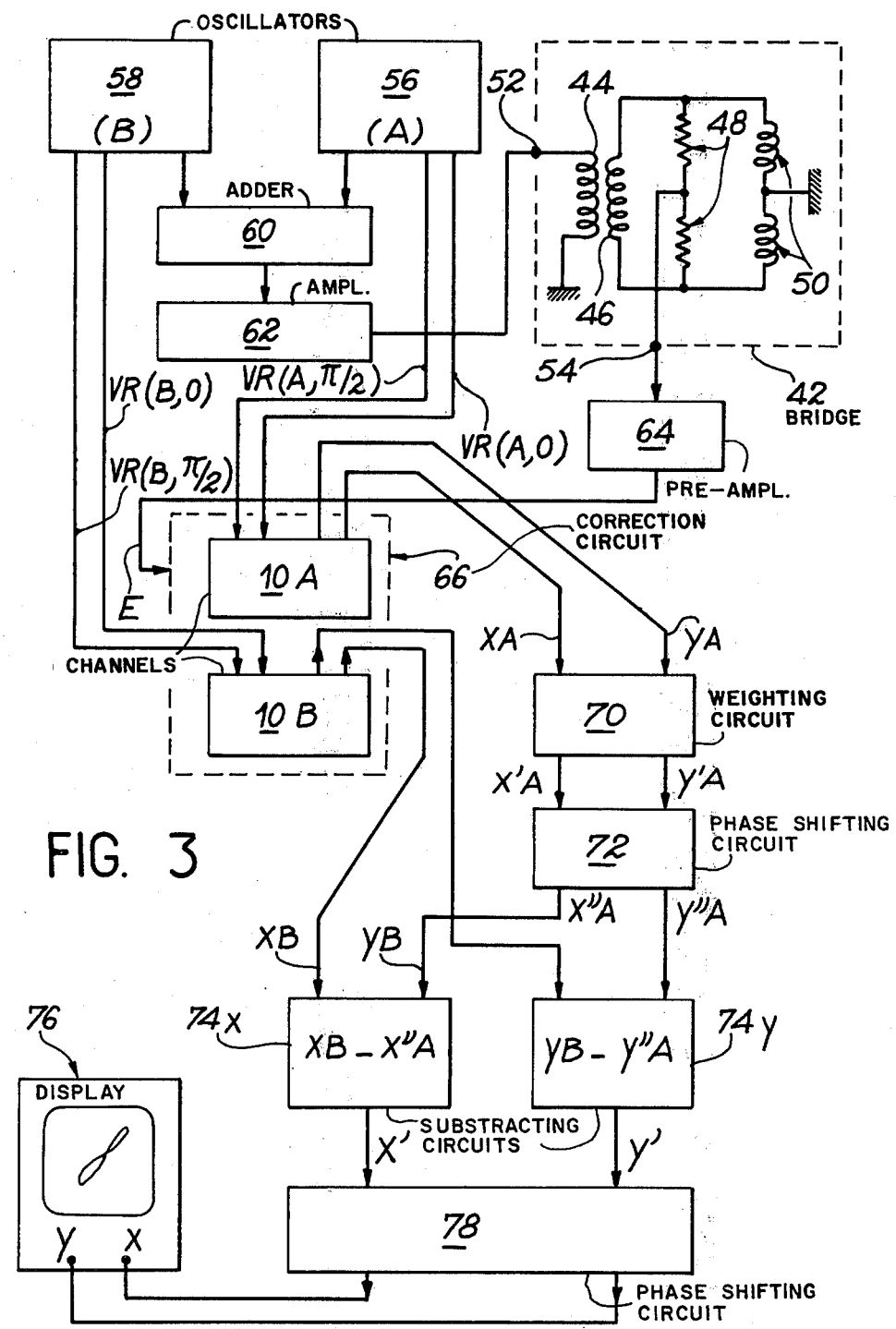

Further features and advantages of the present invention will appear from the following description, given merely by way of example with reference to the accompanying drawing, in which FIG. 1 is a general diagrammatic view of the circuit according to the invention;

FIG. 2 illustrates a possible application of the circuit according to the invention to a balancing circuit for an eddy-current non-destructive testing device; and FIG. 3 illustrates a possible application of the invention to a corrective circuit for an eddy-current non-destructive testing installation.

In all the improved systems for testing by means of eddy-currents, the measuring probe is energized by a multi-frequency signal. It is thus possible to eliminate a few parameters that are considered are undesirable, and to maintain, in the curve illustrating the variations of the signal delivered by said probe, only those portions representing the defects or flaws to be detected. Reference may be had, as regards such a technique, to French patent application No. EN 75 27615, filed on the 9th Sept. 1975, entitled: "an eddy-current non-destructive testing method and a device therefor, making use for a multi-frequency energization and permitting to eliminate a few parameters."

In the following description, it will be assumed, merely in an explanatory way, that the energization of the pick-up, the output signal of which is to be corrected, is carried out according to said multi-frequency technique. Quite obviously, however, the circuit according to the invention will find an application, even a preferable one, in the case where the pick-up to be corrected operates in mono-frequency.

The circuit shown in FIG. 1 corresponds to the particular instance where the signal delivered by the pick-up is a composite signal with two frequencies A and B. Said signal ($V_e$) is applied to one inlet E of the corrective circuit. Said circuit comprises two channels 10A and 10B respectively, for correcting frequency component A and frequency component B respectively. Since these two channels are similar, only one of them has to be described, e.g. the one corresponding to frequency A.

Said channel 10a comprises:

(a) a band-pass filter 12 centered to frequency A, followed by an adjustable amplifier 14;

(b) an analyzer 16 fed by the reference voltage $V_R$ (A,O) with a frequency A and a voltage $V_R$ (A,$\pi/2$) having the same frequency A, but in phase-quadrature with said reference voltage, on the one hand, and by the filtered amplified voltage, on the other hand; said analyzer is provided with two outlets 18X an 18Y for two DC voltages $X_A$ and $Y_A$; said voltages are proportional to the two components of said signals with frequency A, in phase and in phase-quadrature with reference-voltage $V_R(A,O)$, respectively;

(c) a first stage 22X for the treatment of voltage X, said stage being operated by a switch 20X. Said first stage is constituted by a threshold comparator 24X fed by voltage X. Its threshold is determined by an adjustment means (not shown) and it can be zero. The outlet of said comparator is connected to a counter-back counter 26X fed by a clock 27. Said counter-back counter is followed by digital-analog converter 28X connected to a multiplieur 30X with two inlets and one outlet, one of said inlets being fed by said reference voltage $V_R$ (A,O) at frequency A, while the other inlet is connected to converter 28X;

(d) a second stage 22Y for the treatment of voltage Y, said stage being operated by a switch 20Y. Said second stage, like the first one, is constituted by a threshhold comparator 24Y with an inlet fed by voltage Y and an outlet connected to a counter-back counter 26Y, fed by clock 27. Said counter-back counter is followed by a digital-analog converter 28Y, the latter being connected to a multiplier 30Y provided with two inlets and one outlet, one of said inlets being fed by voltage $V_R(A,\pi/2)$ in phase-quadrature with reference voltage $V_R(A,O)$, while the other inlet is connected to said converter;

(e) an adder 32 with two inlets and one outlet, one of said inlets being connected to the outlet of first stage multiplier 30X, while the other inlet is connected to the outlet of second stage multiplier 30Y. The outlet of said adder is connected to a 180° phase-shifter 34 delivering a voltage $V_c$ added to inlet voltage $V_e$ by the adder 36.

The structure of channel 10B is similar, with the only difference that it is fed by a reference signal $V_R(B,O)$, at frequency B, and a signal in phase-quadrature $V_R(B,\pi/2)$ at said frequency. The corrective signal provided by said second channel is fed into the inlet by means of adder 36.

The above circuit operates as follows:

Band-pass filter 12 serves to filter a band centered to frequency A, in the signal applied to the circuit inlet. Said filter is preferably a high-slope filter, e.g. 24 decibels per octave. The thus-filtered signal is subsequently amplified by amplifier 14, then analized in circuit 16. The latter is constituted, for instance, by a memory sampler 17 fed by voltage $V_R(A,O)$ and voltage $V_R(A,\pi/2)$ and by two low-pass filters 19X and 19Y for eliminating the residual background noise resulting from the sampling operation. Such a circuit is conventional. At its outlet terminals 18X and 18Y, it delivers voltages X and Y proportional to the components in phase and in phase-quadrature with reference signal $V_R(A,O)$, respectively.

Switches 20X and 20Y are initially closed and comparators 24X and 24Y are fed by voltages X and Y. They are adapted to deliver a binary signal, the value of which controls the counting or the back counting in counters-back counters 26X and 26Y. So long as signals X and Y have not reached the threshold of comparators 24X and 24Y (said thresholds being possibly zero), the pulses of clock 27 are counted or back counted (according as X and Y are positive or negative) in the counters-back counters.

When the pick-up delivering input voltage $V_e$ is not disturbed, said signal only contains that portion due to the pick-up unbalance. Accordingly, the contents of counters-back counters 26X and 26Y reveal the components X and Y of the unbalance signal at frequency A. These digital contents are transformed into DC voltages by converters 28X and 28Y, then into A.C. voltages at frequency A by multipliers 30X and 30Y.

Adder 32 reconstitutes an overall A.C. voltage; the latter being subsequently phase-shifted by 180° by means of circuit 34, so as to constitute corrective voltage $V_c$. The latter voltage is added to input $V_e$.

In other words, the circuit as shown constitutes a feedback loop, permitting to re-inject a corrective voltage $V_c$ at the circuit inlet, said voltage being opposed to input voltage $V_e$, until $V_e + V_c$ is zero.

The velocity at which the above described circuit is capable of correcting the input voltage (namely, the so-called "balancing" velocity), is a function of the magnitude of reference voltages $V_R$ (A,O) and $V_R(A,\pi/2)$ and of the frequency of clock 27. The latter parameter permits to modify said velocity very easily.

When equilibrium has been reached, i.e. when voltages X and Y are zero, switches 20X and 20Y are open. Counters 26X and 26Y keep the digital contents they had at equilibrium. Said digital contents, once transformed into analog values by means of converters 28X and 28Y, permit to maintain at the circuit inlet the appliction of an appropriate corrective voltage $V_c$ that exactly makes up for the pick-up unbalance. The measuring signals $X_A$ and $Y_A$ delivered by analyser 16 are therefore devoid of that portion due to the pick-up unbalance. Said signals can subsequently be forwarded to other measurement and treatment devices.

The circuit just described illustrates the invention essential means. Such as shown in FIG. 1, it has the drawback of requiring the operator's intervention to determine when the equilibrium comes to an end and to gradually increase the gains up to the desired values. FIG. 2 illustrates a possible embodiment of a circuit exempt from such a drawback.

The circuit as shown in FIG. 2, in addition to those parts already represented in FIG. 1, designated by the same reference numerals, comprises: a circuit 80 for the detection of peaks; a comparator 82, a monostable flip-flop circuit 84; a logical gate 86; an automatic gain control circuit 88; a connection 90 issuing from gate 86 and directed towards the other treatment channels; a connection 92 at the outlet of circuit 88, directed towards the variable gain circuit 14 and, a connection 94 for connecting said amplifier to circuit 88; a connection 93 for connecting circuit 88 to a logical gate 98 of the AND-type, the latter being fed, at two other inlets, by the signals delivered by circuits 24X and 24Y, a logical gate of the AND-type (100), connected to the outlet of gate 98 and also to the outlets of the corresponding gates contained in the other treatment channels; a monostable flip-flop circuit 102; a bistable flip-flop 104 with a resetting-inlet, an outlet S and an extra outlet $\overline{S}$; a balancing push-button 106, a resetting push-button 108; a luminous spy 110 connected to the outlet to bistable flip-flop 104, the latter controlling clock 27; finally a luminous spy 112 connected to the outlet of logical gate 98.

The operation of said circuit lies on the adjustment of amplifier 14, the gain of which is controlled from the outside to a maximum or a minimum value, or automatically according to the voltage at the outlet thereof. Whenever push-button 106 is actuated, bistable flip-flop 104, at its outlet S, delivers a signal that lights up spy 110, indicating that the balancing operation is proceeding. Through its outlet $\overline{S}$, bistable flip-flop 104 controls automatic gain conrol circuit 88 and, when the signal is at logical level 1 at said outlet $\overline{S}$, amplifier 14 is at its maximum gain, possibly 50 dB. Clock 27 is disengaged by bistable flip-flop 104.

In order to prevent pre-amplifier 36, common to all the balancing circuits, from being saturated, peak detector 80, folowed by comparator 82, indicates the magnitude of the signal at the outlet of said pre-amplifier 36. If said signal is too large, gate 86, disengaged by means of monostable flip-flop circuit 84 during the equilibrium period, orders a unit-gain to all amplifiers 14. A pre-balancing operation is then carried out according to the above-described procedure. It follows that the output voltage of pre-amplifier 36 decreases until all the channels are balanced. Then the gain-control of amplifier 14 is disengaged, and each of said channels is in a position to find its own equilibrium independently from the other channels. The gain is thus monitored and gradually increases according to the outlet voltage.

The means permitting such a monitoring are well known. They consist, for instance, of a system with a bulb and a photo-resistor, the outlet voltage of which is used for energizing a bulb acting on a photoresistor that bypasses the amplifier to be controled.

Once the maximum gain has been reached, a signal is applied by connection 96 to logical gate 98, simultaneously with the signals delivered by circuits 24X and 24Y ; a signal is then applied to the second logical gate 100. Once all the channels are balanced, said second logical gate is fed, at all the inlets thereof, by a signal indicating that the balancing operation is over. The outlet of said gate thus delivers a signal for the control of monostable flip-flop circuit 102, which permits to maintain such an equilibrium state for a sufficient period of time. Bistable flip-flop 104 is then reset by monostable flip-flop 102 and bulb 110 is switched off. Should any difficulty arise (e.g. a defective pick-up), such a stop of the balancing operation can be obtained at any moment by means of push-button 108. Spy 112 provides an indication of the equilibrium on each of the channels.

In the circuit shown in FIG. 3 illustrating, as mentioned above, an application of the present invention to a corrective circuit for an eddy-current non-destructive control installation, a measuring bridge 42 constituted by a first coil 44 coupled with a second coil 46, in a bridge mounting comprising two resistors 48 and two inductors 50. Said bridge is provided with one inlet 52 and one outlet 54. The means for energizing such a bridge comprise a first oscillator 56, delivering a current at a frequency A, and a second oscillator 58, delivering a current at a frequency B. These currents delivered by these two oscillators are superimposed in an adding circuit 60 followed by an amplifier 62. The outlet of said amplifier is connected to bridge inlet 52.

The measuring signal is delivered by an outlet 54 of said bridge. Said signal is pre-amplified by a pre-amplifying circuit 64, in order that its level be sufficient for carrying out the balancing operation. Said operation is carried out by a circuit 66 according to the invention, comprising two channels 10A and 10B, corresponding to frequencies A and B, respectively. That circuit is connected to oscillators 56 and 58, from which it receives the required reference signals, viz. $V_R(A,O)$ and $V_R(B,O)$ for those signals in phase with the energization, and $V_R(A,\pi/2)$ and $V_R(B,\pi/2)$ for those signals in phase-quadrature, the former being forwarded to channel 10A, while the latter are forwarded to channel 10B.

Corrective circuit 66 delivers the resistive portions $X_A$ and the reactive portions $Y_A$ of the component at frequency A, and the resistive portions $X_B$ and the reactive portions $Y_B$ of the component at frequency B, these portions being exempt from those signals due to the bridge unbalance. The voltages involved are DC voltages varying according to the bridge movements when the latter passes in the vicinity of a defect, or flaw, of the part under control. These voltages are directed towards a cancelling circuit comprising a weighting circuit 70 on the channel corresponding to frequency A. Said circuit is adapted to multiply portions $X_A$ and $Y_A$, by appropriate respective coefficients, and it delivers voltages $X'_A$ and $Y'_A$ such that modulus $$\sqrt{X_A^2 + Y_A^2}$$

for the signal corresponding to a parameter to be eliminated, be equal to modulus $$\sqrt{X_b^2 + Y_B^2}$$

of the signal corresponding to the same parameter, at frequency B. Weighting circuit 70 is followed by a phase-shifting circuit 72, adapted to modify voltages $X'_A$ and $Y'_A$ and to deliver new voltages $X''_A$ and $Y''_A$ such that, as regards the defect of the parameter to be eliminated, these new voltages be equal to voltages $X_B$ and $Y_B$ and corresponding to frequency B.

Substracting circuit 74X and 74Y subsequently carry out the difference between voltages $X_B$ and $X''_A$ and voltages $Y_B$ and $Y'''_A$. At the outlet of circuits 74X and 74Y are available two new voltages X' and Y', from which the undesirable parameter has been eliminated. These portions are precisely applied to vizualizing means 76, possibly after having passed through a phase-shifting circuit 78, said circuit permitting to direct the curves obtained.

For more detailed information regarding such a specific application, reference may be had to the above-mentioned French patent application.

What is claimed is:

1. In a circuit for automatically correcting an electric signal given by a differential pick-up likely to have a slight unbalance, said signal having a given frequency and containing a portion resulting from such unbalance, means for determining said portion and subtracting it from the signal given by said pick-up, said means comprising:

(a) a band-pass filter centered to said given frequency, followed by an adjustable gain amplifier;
   (b) an analyzer fed by a reference voltage at said frequency and by a voltage in phase-quadrature and by the voltage delivered by said band-pass filter, said analyzer comprising a sampler fed by said reference signal and by said signal in phase-quadrature, said sampler having two outputs and two low-pass filters connected to said two outputs, said analyzer delivering two DC-voltages X and Y proportional to the two components of the voltage delivered by said band-pass filter which are respectively in phase and in phase-quadrature with respect to said reference-voltage;
   (c) a first stage comprising: a threshold comparator fed by voltage X; a counter-back counter connected to said comparator; a clock for feeding said counter-back counter; a digital-analog converter connected to said counter; a multiplier with two inlets and one outlet, one of said inlets being fed by said reference voltage, while the other is connected to said converter;
   (d) a second stage comprising: a threshold comparator fed by voltage Y; a counter-back counter connected to said comparator; a clock for feeding said counter-back counter, a digital-analog converter connected to said counter-back counter; a multiplier with two inlets and one outlet, one of said inlets being fed by said voltage in phase-quadrature with respect to said reference-voltage, while the other inlet is connected to said converter;
   (e) an adder with two inlets and one outlet, one of said inlets being connected to the first stage multiplier outlet, while the other inlet is connected to the second stage multiplier outlet, the outlet of said adder being connected to the circuit inlet by mans of a phase inverter in common for all said channels.

2. In a circuit for automatically correcting an electric signal given by a differential pick-up likely to have a slight unbalance, said signal having a given frequency and containing a portion resulting from such unbalance, means for determining said portion and subtracting it from the signal given by said pick-up, said means comprising:

(a) a band-pass filter centered to said given frequency followed by an adjustable gain amplifier;
   (b) an analyzer fed by a reference voltage at said frequency and by a voltage in phase-quadrature and by the voltage delivered by said band-pass filter, said analyzer comprising a sampler fed by said reference signal and by said signal in phase-quadrature, said sampler having two outputs and two low-pass filters connected to said two outputs, said analyzer delivering two DC-voltages X and Y proportional to the two components of the voltage delivered by said band-pass filter which are respectively in phase and in phase-quadrature with respect to said reference-voltage;
   (c) a first stage comprising: a threshold comparator fed by voltage X, a counter-back counter connected to said comparator; a clock for feeding said counter-back counter; a digital-analog converter connected to said counter; a multiplier with two inlets and one outlet, one of said inlets being fed by said reference voltage, while the other is connected to said converter;
   (d) a second stage comprising: a threshold comparator fed by voltage Y; a counter-back counter connected to said comparator; a clock for feeding said counter-back counter, a digital-analog converter connected to said counter-back counter; a multiplier with two inlets and one outlet, one of said inlets being fed by said voltage in phase-quadrature with respect to said reference-voltage, while the other inlet is connected to said converter;
   (e) an adder with two inlets and one outlet, one of said inlets being connected to the first stage multiplier outlet, while the other inlet is connected to the second stage multiplier outlet, the outlet of said adder being connected to the circuit inlet by means of a phase inverter in common for all said channels;
   (f) means for controlling the gain of said adjustable gain amplifier at a maximum value and at a minimum value and at a value depending on the voltage at the outlet thereof, said means comprising a peak pick-up connected to the circuit inlet, a comparator connected to said pick-up, a monostable flip-flop circuit, a logical gate with two inlets and one outlet, connected to a circuit for automatically controlling the gain of said amplifier, a logical gate of the AND-type with three inlets, one of which is connected to said circuit for controlling the gain while the other two are connected to the outlets of said threshold comparator circuits, a single AND-gate with as many inlets as there are channels, said inlets being connected to said AND-gates with three inlets belonging to each of said channels, a monostable circuit connected to said single AND-gate, and a bistable flip-flop provided with a resetting inlet and two extra outlets, one of which is connected to said circuit for automatically controlling the gain, while the other is connected to said logical gate with two inlets.

* * * * *

UNITED STATES PATENT AND TRADEMARK OFFICE
CERTIFICATE OF CORRECTION

PATENT NO. : 4,326,166
DATED : April 20, 1982
INVENTOR(S) : Michel Pigeon et al

It is certified that error appears in the above-identified patent and that said Letters Patent are hereby corrected as shown below:

Item [30] Foreign Application Priority Data should read:

Dec. 7, 1978 [FR] France........ 7834478

Signed and Sealed this

Fifteenth Day of June 1982

[SEAL]

Attest:

GERALD J. MOSSINGHOFF

Attesting Officer    Commissioner of Patents and Trademarks